US008594507B2

(12) United States Patent
Youngner et al.

(10) Patent No.: US 8,594,507 B2
(45) Date of Patent: *Nov. 26, 2013

(54) METHOD AND APPARATUS FOR MEASURING GAS CONCENTRATIONS

(75) Inventors: Daniel Youngner, Maple Grove, MN (US); Lisa Lust, Minneapolis, MN (US)

(73) Assignee: Honeywell International Inc., Morristown, NJ (US)

( * ) Notice: Subject to any disclaimer, the term of this patent is extended or adjusted under 35 U.S.C. 154(b) by 203 days.

This patent is subject to a terminal disclaimer.

(21) Appl. No.: 13/162,119

(22) Filed: Jun. 16, 2011

(65) Prior Publication Data

US 2012/0318041 A1 Dec. 20, 2012

(51) Int. Cl.
*H04B 10/00* (2013.01)
(52) U.S. Cl.
USPC .......................... 398/132; 398/138; 398/133
(58) Field of Classification Search
USPC .................................................. 398/132–139
See application file for complete search history.

(56) References Cited

U.S. PATENT DOCUMENTS

| | | | | |
|---|---|---|---|---|
| 3,622,791 A * | 11/1971 | Bernard | ...................... | 250/231.19 |
| 3,668,404 A * | 6/1972 | Lehovec | ...................... | 250/552 |
| 3,705,308 A * | 12/1972 | Lehovec | ...................... | 250/552 |
| 4,412,105 A * | 10/1983 | Muscatell | ...................... | 381/172 |
| 4,422,182 A * | 12/1983 | Kenjyo | ...................... | 398/132 |
| 4,479,265 A * | 10/1984 | Muscatell | ...................... | 398/134 |
| 4,740,086 A * | 4/1988 | Oehler et al. | ...................... | 356/432 |
| 4,805,985 A * | 2/1989 | Fleck | ...................... | 385/12 |
| 5,146,083 A * | 9/1992 | Zuckerwar et al. | ...................... | 250/227.21 |
| 5,200,610 A * | 4/1993 | Zuckerwar et al. | ...................... | 250/227.21 |
| 5,262,884 A * | 11/1993 | Buchholz | ...................... | 398/134 |
| 5,333,205 A * | 7/1994 | Bogut et al. | ...................... | 381/172 |
| 5,910,855 A * | 6/1999 | Thomas | ...................... | 359/285 |
| 5,933,245 A * | 8/1999 | Wood et al. | ...................... | 356/437 |
| 5,969,838 A * | 10/1999 | Paritsky et al. | ...................... | 398/136 |

(Continued)

FOREIGN PATENT DOCUMENTS

| | | |
|---|---|---|
| DE | 29922312 U1 | 3/2000 |
| DE | 102006006302 A1 | 8/2007 |
| EP | 1371956 A1 | 12/2003 |

OTHER PUBLICATIONS

"U.S. Appl. No. 13/162,169, Non Final Office Action mailed Feb. 28, 2013", 15 pgs.

(Continued)

*Primary Examiner* — Agustin Bello
(74) *Attorney, Agent, or Firm* — Schwegman, Lundberg & Woessner, P.A.

(57) ABSTRACT

Some embodiments are directed to a photoacoustic sensor. The photoacoustic sensor may comprise: a gas cell with an opening; a light source to generate to radiate a sample gas within the gas cell; an optical microphone to detect the sample gas within the gas cell; and a membrane aligned with the opening of the gas cell to permit sample gas to enter the gas cell. The optical microphone includes a semiconducting laser. The semiconducting laser includes a p-n junction within a cavity of the semiconducting laser. The optical microphone further includes a pressure-sensitive membrane that receives coherent light emitted from the semiconducting laser and directs reflected light back toward the semiconducting laser. During operation of the optical microphone, the pressure-sensitive membrane flexes in response to acoustic pressure waves. The phase of the reflected light is dependent upon a distance of the pressure-sensitive membrane from an aperture of the semiconducting laser.

19 Claims, 4 Drawing Sheets

(56) References Cited

U.S. PATENT DOCUMENTS

| | | | |
|---|---|---|---|
| 5,995,260 A * | 11/1999 | Rabe | 398/115 |
| 6,014,239 A * | 1/2000 | Veligdan | 398/134 |
| 6,055,080 A * | 4/2000 | Furstenau et al. | 398/139 |
| 6,147,787 A * | 11/2000 | Veligdan | 398/133 |
| 6,154,551 A * | 11/2000 | Frenkel | 381/172 |
| 6,233,045 B1 | 5/2001 | Suni et al. | |
| 6,301,034 B1 * | 10/2001 | Speciale | 398/134 |
| 6,301,968 B1 * | 10/2001 | Maruyama et al. | 73/657 |
| 6,323,943 B1 * | 11/2001 | Maruyama et al. | 356/28.5 |
| 6,459,798 B1 * | 10/2002 | Paritsky et al. | 381/172 |
| 6,483,619 B1 * | 11/2002 | Greywall | 398/132 |
| 6,567,572 B2 * | 5/2003 | Degertekin et al. | 385/12 |
| 6,590,661 B1 * | 7/2003 | Shnier | 356/432 |
| 6,662,627 B2 * | 12/2003 | Arnott et al. | 73/24.02 |
| 6,671,638 B2 * | 12/2003 | Kitazumi et al. | 702/75 |
| 6,707,027 B2 * | 3/2004 | Liess et al. | 250/221 |
| 6,721,429 B1 * | 4/2004 | Akamatsu et al. | 381/122 |
| 6,759,671 B2 * | 7/2004 | Liess et al. | 250/559.32 |
| 7,114,395 B2 * | 10/2006 | Miyazawa et al. | 73/655 |
| 7,202,942 B2 * | 4/2007 | Deines | 356/28.5 |
| 7,224,465 B2 * | 5/2007 | Balachandran et al. | 356/480 |
| 7,277,642 B2 * | 10/2007 | Shinzou | 398/133 |
| 7,355,720 B1 * | 4/2008 | Carr | 356/498 |
| 7,359,067 B2 * | 4/2008 | Carr | 356/519 |
| 7,391,976 B2 * | 6/2008 | Kobayashi et al. | 398/133 |
| 7,440,117 B2 * | 10/2008 | Degertekin et al. | 356/521 |
| 7,485,847 B2 * | 2/2009 | Degertekin et al. | 250/237 G |
| 7,495,775 B2 * | 2/2009 | Carr | 356/519 |
| 7,561,277 B2 * | 7/2009 | Chin et al. | 356/480 |
| 7,630,589 B2 * | 12/2009 | Kilic et al. | 385/12 |
| 7,738,116 B2 * | 6/2010 | Kauppinen | 356/502 |
| 7,765,871 B2 * | 8/2010 | Riddle | 73/590 |
| 7,787,725 B2 * | 8/2010 | Kahana et al. | 385/31 |
| 7,894,618 B2 * | 2/2011 | Carr | 381/172 |
| 7,961,897 B2 * | 6/2011 | Weigold | 381/174 |
| 7,995,193 B2 * | 8/2011 | Kuwata | 356/27 |
| 8,050,569 B2 * | 11/2011 | Habberstad et al. | 398/118 |
| 8,085,403 B2 * | 12/2011 | Fritz et al. | 356/437 |
| 8,096,165 B2 * | 1/2012 | Crane | 73/24.02 |
| 8,302,461 B2 * | 11/2012 | Angster et al. | 73/31.04 |
| 8,306,429 B2 * | 11/2012 | Hashimoto et al. | 398/132 |
| 8,379,206 B2 * | 2/2013 | Kachanov et al. | 356/436 |
| 2001/0043378 A1 * | 11/2001 | Paritsky | 359/149 |
| 2002/0080982 A1 * | 6/2002 | Paritsky et al. | 381/172 |
| 2002/0080983 A1 * | 6/2002 | Paritsky et al. | 381/172 |
| 2002/0181049 A1 * | 12/2002 | Paritsky et al. | 359/150 |
| 2003/0002129 A1 * | 1/2003 | Kobayashi et al. | 359/285 |
| 2003/0007890 A1 * | 1/2003 | Mitani et al. | 422/56 |
| 2003/0039368 A1 * | 2/2003 | Paritsky et al. | 381/58 |
| 2004/0069939 A1 * | 4/2004 | Paritsky et al. | 250/231.1 |
| 2004/0071383 A1 * | 4/2004 | Balachandran et al. | 385/12 |
| 2004/0151417 A1 * | 8/2004 | Lagakos et al. | 385/12 |
| 2004/0170086 A1 * | 9/2004 | Mayer et al. | 367/178 |
| 2005/0018541 A1 * | 1/2005 | Johansen et al. | 367/149 |
| 2005/0041905 A1 * | 2/2005 | Lagakos et al. | 385/12 |
| 2005/0052724 A1 * | 3/2005 | Suzuki et al. | 359/305 |
| 2005/0157901 A1 * | 7/2005 | Hatano et al. | 381/356 |
| 2005/0163509 A1 * | 7/2005 | Kobayashi et al. | 398/132 |
| 2005/0241398 A1 * | 11/2005 | Suzuki et al. | 73/643 |
| 2006/0072887 A1 * | 4/2006 | Lagakos et al. | 385/117 |
| 2006/0072888 A1 * | 4/2006 | Lagakos et al. | 385/117 |
| 2006/0181712 A1 * | 8/2006 | Degertekin et al. | 356/505 |
| 2006/0192976 A1 * | 8/2006 | Hall et al. | 356/505 |
| 2007/0028695 A1 * | 2/2007 | Suzuki et al. | 73/655 |
| 2007/0041597 A1 * | 2/2007 | Song | 381/175 |
| 2007/0058157 A1 * | 3/2007 | Deines | 356/28 |
| 2007/0084265 A1 * | 4/2007 | Haveri | 73/25.02 |
| 2007/0165896 A1 | 7/2007 | Miles et al. | |
| 2007/0215798 A1 * | 9/2007 | Kauppinen | 250/231.1 |
| 2007/0236704 A1 * | 10/2007 | Carr | 356/519 |
| 2007/0269059 A1 * | 11/2007 | Akino et al. | 381/170 |
| 2008/0034866 A1 * | 2/2008 | Kilic et al. | 73/514.26 |
| 2008/0049230 A1 * | 2/2008 | Chin et al. | 356/480 |
| 2008/0075404 A1 * | 3/2008 | Chin et al. | 385/12 |
| 2008/0134756 A1 * | 6/2008 | Riddle | 73/24.02 |
| 2008/0151348 A1 * | 6/2008 | Carr | 359/239 |
| 2009/0123112 A1 * | 5/2009 | Kahana et al. | 385/13 |
| 2009/0208163 A1 * | 8/2009 | Kilic et al. | 385/12 |
| 2009/0211838 A1 * | 8/2009 | Bilan | 181/131 |
| 2010/0092125 A1 * | 4/2010 | Kilic et al. | 385/11 |
| 2010/0103425 A1 * | 4/2010 | Miklos et al. | 356/438 |
| 2010/0139405 A1 * | 6/2010 | Melikechi et al. | 73/655 |
| 2010/0275675 A1 * | 11/2010 | Seppa et al. | 73/24.01 |
| 2010/0321698 A1 * | 12/2010 | Santhanakrishnan et al. | 356/446 |
| 2011/0038492 A1 * | 2/2011 | Ronald et al. | 381/172 |
| 2011/0041616 A1 * | 2/2011 | Kilic et al. | 73/657 |
| 2011/0088470 A1 * | 4/2011 | Kilic et al. | 73/514.26 |
| 2011/0170117 A1 * | 7/2011 | Fischer | 356/519 |
| 2011/0239621 A1 * | 10/2011 | Meneely et al. | 60/39.281 |
| 2011/0268384 A1 * | 11/2011 | Akkaya et al. | 385/12 |
| 2012/0318041 A1 * | 12/2012 | Youngner et al. | 73/24.02 |
| 2012/0321322 A1 * | 12/2012 | Lust et al. | 398/133 |

OTHER PUBLICATIONS

"European Application Serial No. 12170371.4, European Search Report mailed Sep. 5, 2012", 3 pgs.

"European Application Serial No. 12170371.4, Office Action mailed Oct. 15, 2012", 6 pgs.

"European Application Serial No. 12170371.4, Response filed Feb. 14, 2013 to Examination Notification Art. 94(3) mailed Oct. 15, 2012", 7 pgs.

* cited by examiner

METHOD AND APPARATUS FOR MEASURING GAS CONCENTRATIONS

TECHNICAL FIELD

Embodiments relate to a photoacoustic sensor. More specifically, embodiments relate to a photoacoustic sensor that includes an optical microphone.

BACKGROUND

The reliability of toxic gas detectors is of great importance in many applications, especially when these instruments are used for ensuring the safety of personnel. Reliability is typically obtained by periodic checking of the instrument response to a test gas, however calibration test gases are typically supplied in large, bulky and expensive gas cylinders.

Potentially hazardous atmospheres are found in many locations, due to the presence of toxic gases, combustible gas mixtures or the excess or deficiency of oxygen concentration. Many types of gas detection instruments have been developed to provide a warning that the atmosphere contains potentially hazardous components, or to initiate remedial action. Examples of these gas detection instruments include the detection of combustible gases in coal mines, hydrogen sulfide in oil fields and water treatment plants, carbon monoxide in places ranging from steel mills to bedrooms, and oxygen in confined spaces, such as sewers. Within each gas detection instrument there are one or more gas sensors, whose function is to provide an electrical signal, which varies in response to the gas concentration.

Photoacoustic sensors may be used to detect sample gases based on the tendency of molecules of sample gases, when exposed to certain frequencies of radiant energy, to absorb the energy and reach higher levels of molecular vibration and rotation thereby to reach a higher temperature and pressure. When the radiant energy is amplitude modulated, the resulting fluctuations in energy available for absorption produce corresponding temperature and pressure fluctuations. A sensitive detector can be used to generate an electrical output representing the pressure fluctuations of the sample gases, which can be analyzed to evaluate properties or attributes of the sample gases.

Many existing photoacoustic sensors utilize commercial MEMs microphones to sense pressure waves on a flexible diaphragm by using capacitive pick off techniques to measure capacitance. Most MEMs microphones typically require the diaphragm to be at least 1.5 mm×1.5 mm×1 mm in size in order to attain a measurable capacitance.

In addition, most MEMs microphones usually require an additional area in order to accommodate an internal amplifier. The amount of additional area that is required to accommodate the internal amplifier typically depends on the complexity of the internal amplifier.

The voltage signals levels that are normally output from a MEMs microphone typically need to be enhanced in order to reach a sufficiently high level (i.e., millivolts) above the voltage signals levels that are associated with ambient noise.

Therefore, a need exists for a photoacoustic sensor that includes a relatively smaller microphone which is able to output voltage signals levels that are above the voltage signal levels that are associated with ambient noise. Making the microphone smaller would thereby permit the overall size and complexity of the photoacoustic sensor to be reduced.

BRIEF DESCRIPTION OF THE DRAWINGS

Some embodiments are illustrated by way of examples, and not by way of limitations, in the figures of the accompanying drawings in which.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Various embodiments described herein utilize photoacoustic gas detection to detect and identify gas samples. One principle of photoacoustic gas detection is based on the measurement of the pressure variation generated in a gas cell or chamber by selective absorption of infrared radiation by the target gas. A measurement includes sampling periods and detecting periods. During detecting, the sample gas in the gas cell may be irradiated with, for example, a modulated narrowband infrared radiation. The sample gas then heats and cools as incident infrared radiation is modulated. Such temperature fluctuations in turn generate pressure waves, which are detected by an optical microphone. The optical microphone generates an output voltage signal, which can be processed and analyzed to identify substances existing in the sample gas and evaluate the properties or attributes, for example the concentration values, of the sample gas collected in the gas cell.

Various embodiments of the application provide a photoacoustic sensor, which includes: a gas cell or chamber having an opening; a light source to generate a radiation to radiate sample gas within the gas cell; an optical microphone to detect the sample gas within the gas cell to generate output voltage signals in response to acoustic signals that are generated by pressure fluctuations of the radiated sample gas caused by the radiation; and a membrane that is aligned with the opening of the gas cell. The membrane permits the sample gas to enter the gas cell.

In some embodiments, the detector collects pressure fluctuations within the ambient environment (i.e., noise) when the light source is not producing radiation to determine spectral content of the pressure fluctuations within the ambient environment. A control receives signals from the detector that represent the spectral content of the pressure fluctuations within the ambient environment. The control adjusts a frequency of the radiation produced by the light source to a frequency that conflicts less with the spectral content of the pressure fluctuations within the ambient environment.

By measuring the acoustic noise signature with the microphone while the IR source inactive, a sensor operating frequency can be selected that minimizes acoustic noise interference. The acoustic noise signature can be measured by adjusting the reference frequency used by the lock-in with the IR source disabled. The operating frequency can be chosen that minimizes the noise content.

In some embodiments, the membrane is replaced with an active valve having a speaker aligned with the opening of the gas cell. The speaker may have a similar or identical structure to a loudspeaker. For example, the speaker may have a permanent magnet, a voice coil, and a diaphragm (or cone) attached to the voice coil. The speaker can be used to control the access of the gas cell by applying a control signal, which can be either an AC control signal or a DC control signal.

Figure 1:
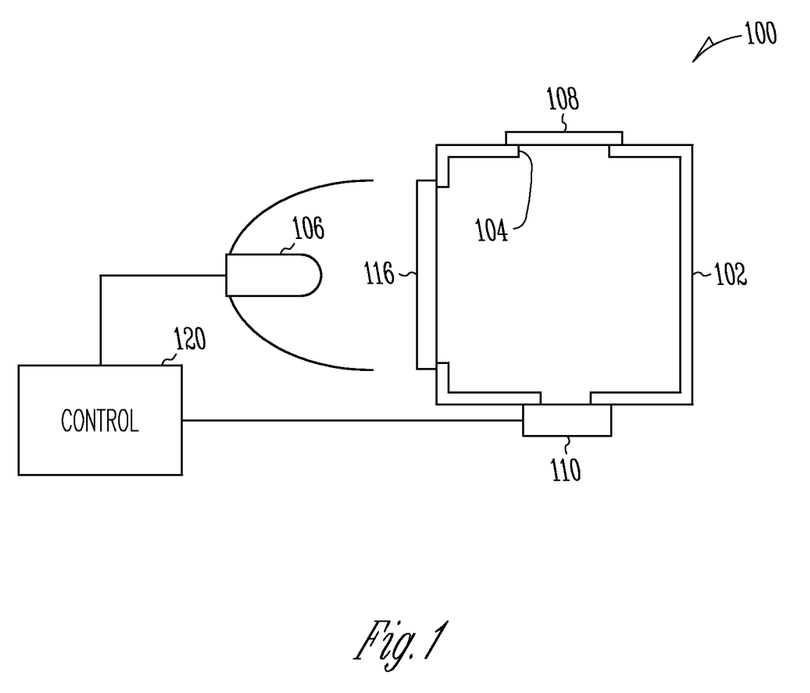
FIG. 1 is a diagram illustrating a photoacoustic sensor according to an example embodiment.

FIG. 1 is a block diagram of a photoacoustic sensor 100 according to an example embodiment. The photoacoustic sensor 100 may comprise: a gas cell 102 with an opening 104; a light source 106 to generate a radiation to radiate sample gas within the gas cell 102; an optical microphone 110 to detect the sample gas within the gas cell 102; and a membrane 108 aligned with the opening 104 of the gas cell 102 to permit sample gas to enter gas cell 102.

Figure 2:
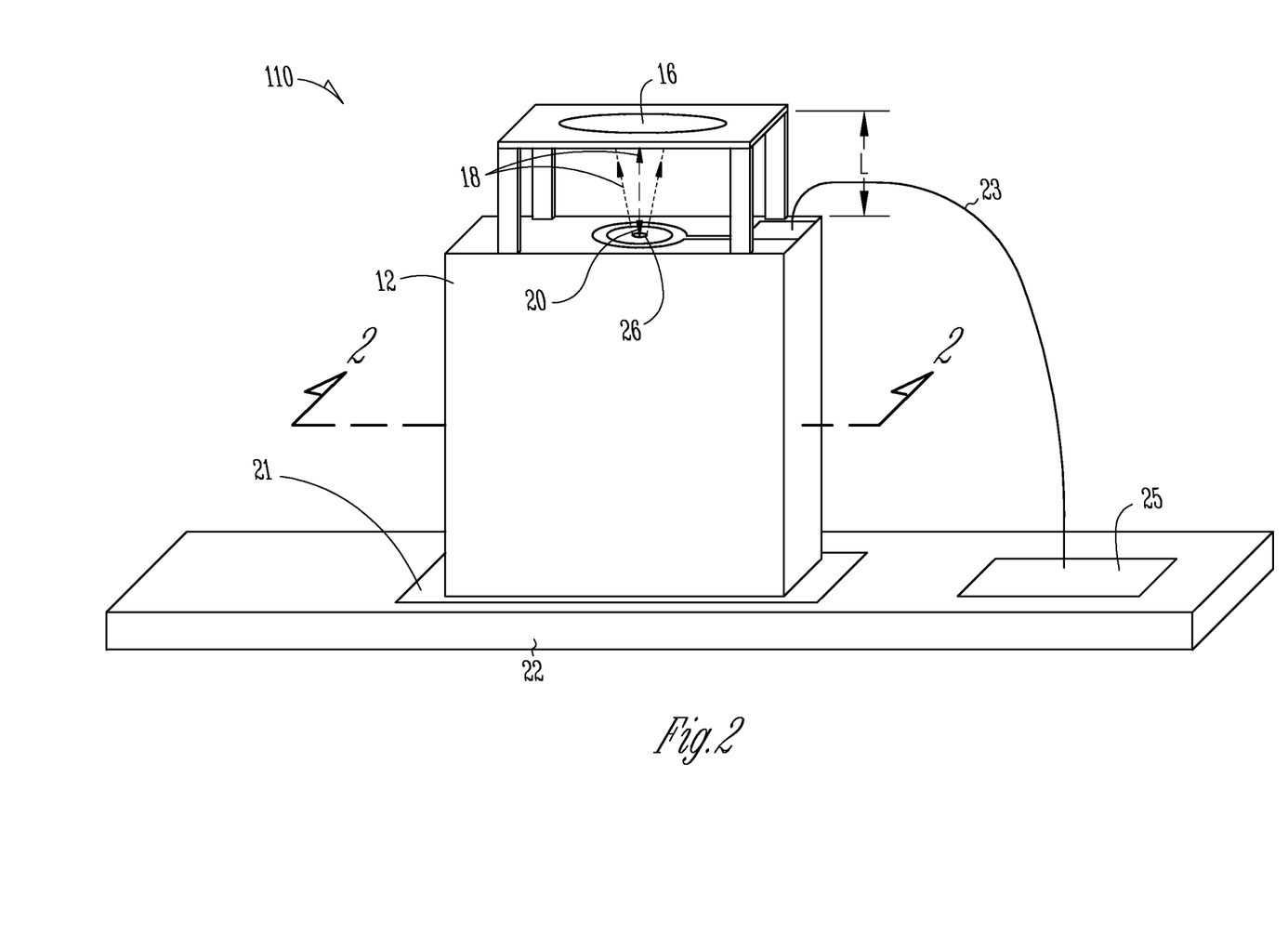
FIG. 2 is a diagram illustrating an optical microphone according to an example embodiment.
Figure 3:
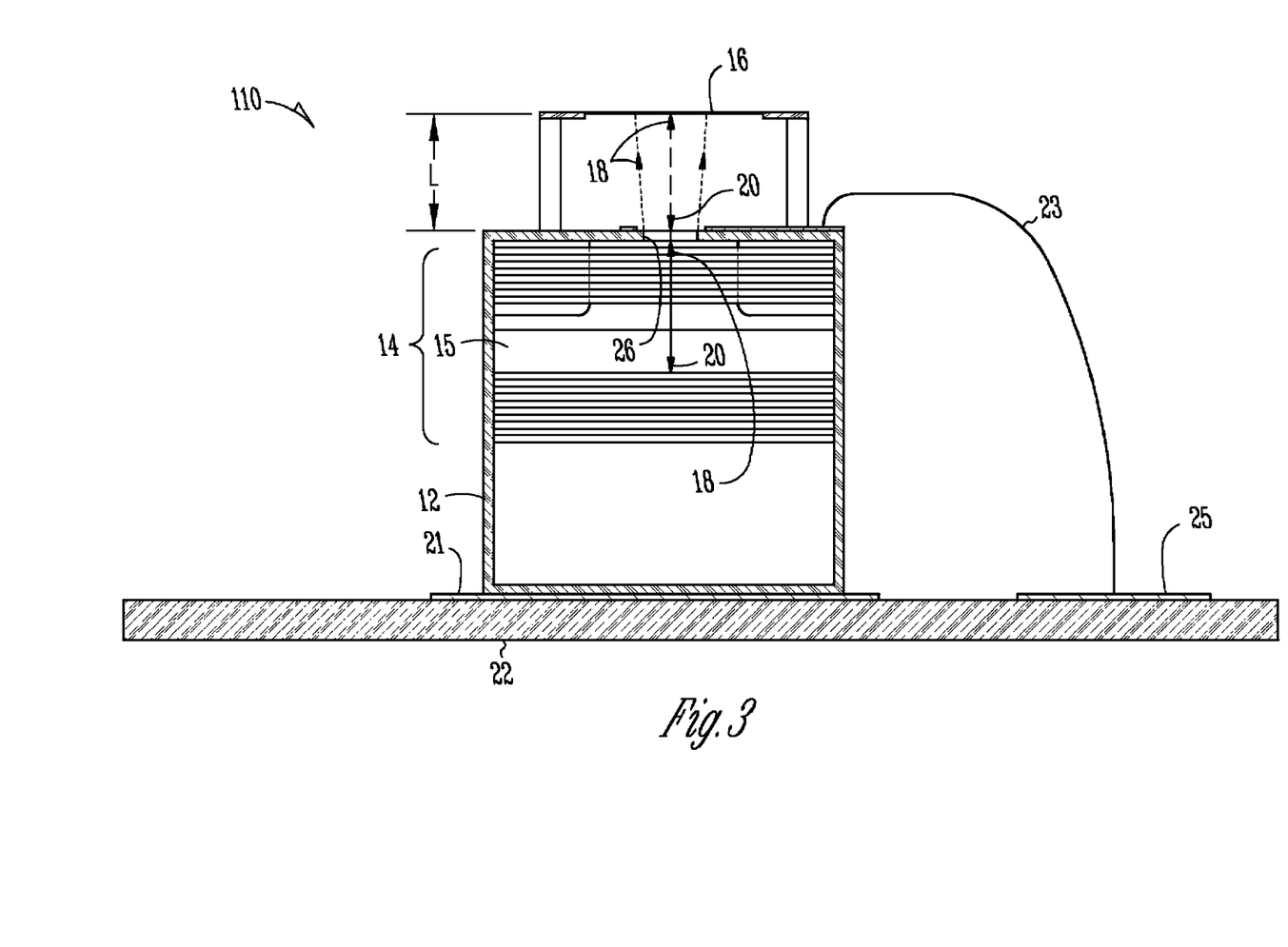
FIG. 3 is a section view of the optical microphone shown in FIG. 2 taken along line 3-3.

FIGS. 2 and 3 are diagrams illustrating an example optical microphone 110. The optical microphone 110 includes a semiconducting laser 12. The semiconducting laser 12 includes a p-n junction 14 within a cavity 15 of the semiconducting laser 12 (see FIG. 3). The optical microphone 110 further includes a pressure-sensitive membrane 16 that receives coherent light 18 emitted from the semiconducting laser 12 and directs reflected light 20 back toward the semiconducting laser 12.

During operation of the optical microphone 110, the pressure-sensitive membrane 16 flexes in response to acoustic pressure waves. The phase of the reflected light 20 is dependent upon a distance L of the pressure-sensitive membrane 16 from an aperture 26 of the semiconducting laser 12.

The type of semiconducting laser 12 that is utilized in the optical microphone 110 will be determined in part based on application requirements. As an example, a low power application would opt to use a semiconducting laser 12 which functions at low threshold currents and voltages. Some example lasers include diode lasers and vertical cavity surface emitting lasers (among other types of lasers that are known now or developed in the future).

As an example, the pressure-sensitive membrane 16 may be formed of silicon dioxide and may include a reflective layer formed of gold. In addition, the pressure-sensitive membrane 16 may include apertures to facilitate an appropriate amount of flexing during exposure to acoustic pressure waves.

In one example embodiment, the pressure-sensitive membrane 16 may be fabricated as part of a MEMs box with rigid silicon walls where the flexible pressure-sensitive membrane 16 is the cover of the box. As an example, the MEMs box may be processed directly over the semiconducting laser 12 such that the pressure-sensitive membrane 16 may be approximately several microns above the lasing aperture 26 (i.e., distance L in the FIGS.).

The pressure-sensitive membrane 16 may be at least moderately (or significantly) reflective at the wavelength of the coherent light 18 that is emitted by the semiconducting laser 12. The modulus of the pressure-sensitive membrane 16 may be critical to fabricating low distortion microphones under a wide dynamic range of sound levels.

In the example embodiment that is illustrated in FIGS. 2 and 3, the semiconducting laser 12 is surface mounted partially, or wholly, onto a ground pad 21 that is formed on a substrate 22. The semiconducting laser 12 may also be wire bonded to a bond pad 25 on the substrate 22 via a bonded wire 23. The bonded wire 23 is able to supply current from a current source to the semiconducting laser 12 in order to power the semiconducting laser 12 and also enable monitoring of the p-n junction 14 voltage.

In some embodiments, the current source supplies power to the semiconducting laser 12 until the semiconducting laser 12 is above a lasing threshold and a voltage is generated at the p-n junction 14 of the semiconducting laser 12. Operating the semiconducting laser 12 at the threshold current may be optimum because the optical feedback generates the largest change in the p-n junction voltage ($\Delta V$).

The coherence of the reflected light 20 superimposed in with the emitted light 18 inside a cavity 15 of the semiconducting laser 12 depends on the phase shift that is introduced in the reflected light 20 by the round trip travel to and from the pressure-sensitive membrane 16. During operation of the optical microphone 110, the reflected light 20 undergoes phase changing as the pressure-sensitive membrane 16 fluctuates due to acoustic pressure waves acting on the pressure-sensitive membrane 16. The voltage level at the p-n junction 14 changes as the reflected light 20 mixes with the coherent light 18 in the cavity 15.

Figure 4:
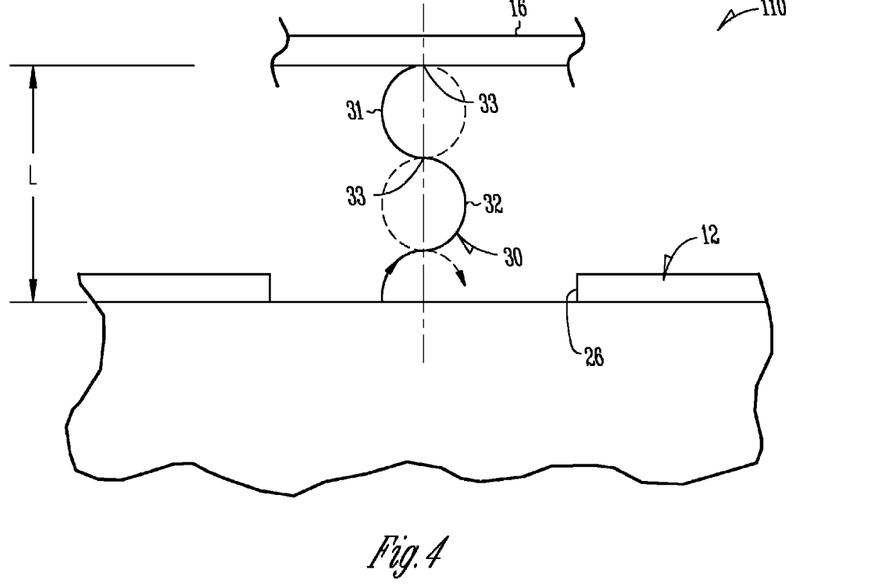
FIG. 4 is an enlarged schematic section view illustrating a portion of the optical microphone shown in FIGS. 2 and 3 where the pressure-sensitive membrane is at an approximately one wave length distance from the aperture of the semiconducting laser.

As shown in FIG. 4, the coherent light 18 is a sinusoidal light wave 30 that includes a maximum 31, a minimum 32 and a midpoint 33 between the maximum 31 and minimum 32. The pressure-sensitive membrane 16 is located at a distance L from the aperture 26 such that the sinusoidal light wave 30 reaches the pressure-sensitive membrane 16 at the midpoint 33 of the sinusoidal light wave 30. FIG. 4 shows the pressure-sensitive membrane 16 at a one wave length distance from the aperture 26. It should be noted that the pressure-sensitive membrane 16 may be located at any integral length distance of the sinusoidal light wave 30 from the aperture 26.

Figure 5:
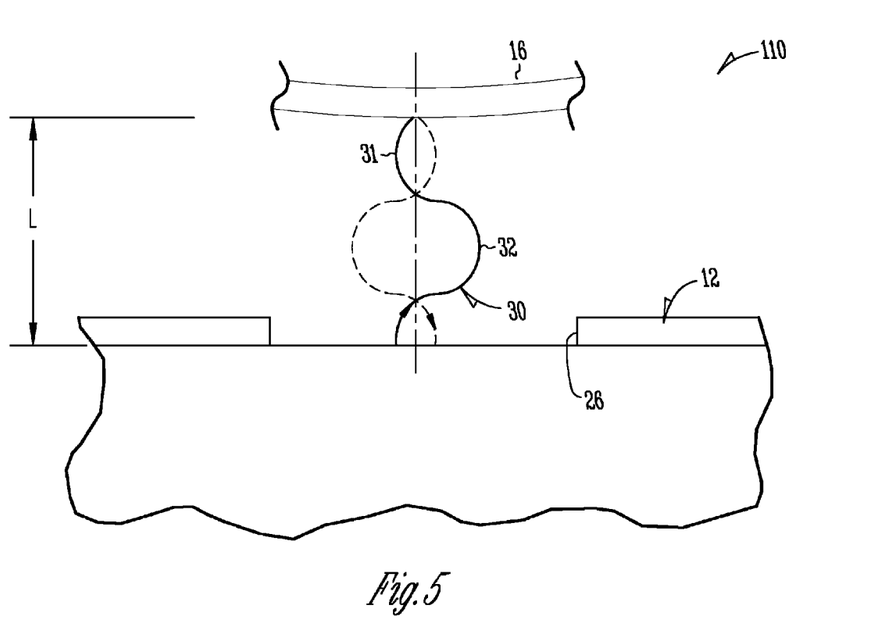
FIG. 5 shows the enlarged schematic section view of FIG. 4 where the pressure-sensitive membrane is fluctuating due to exposure to acoustic pressure waves.

FIG. 5 shows the pressure-sensitive membrane 16 of FIG. 4 where the pressure-sensitive membrane 16 is fluctuating due to pressure waves. This fluctuation of the pressure-sensitive membrane 16 changes the distance L from the apertures 26 to the pressure-sensitive membranes 16 such that the midpoints 33 of the sinusoidal waves 30 no longer reach the respective pressure-sensitive membranes 16.

Therefore, the phase of the reentrant photons into the semiconducting laser 12 depends on the distance L to the pressure-sensitive membrane 16. In the equations below, $\tau$, is the round trip propagation time, c is the speed of light, $\lambda$, is the wavelength, and $\eta$ is a coupling coefficient which is related to the laser cavity parameters.

$$\tau = \frac{2L}{c} \quad \Delta V = \eta \cos\left(\frac{2\pi c \tau}{\lambda}\right) = \eta \cos\left(\frac{4\pi L}{\lambda}\right)$$

As the pressure-sensitive membrane 16 fluctuates due to acoustic pressure changes, the distance L to the pressure-sensitive membrane 16 thereby induces corresponding fluctuations in the p-n junction voltage. In embodiments where the pressure-sensitive membrane 16 is located at any integral length distance of the sinusoidal light wave 30 from the aperture 26, the voltage at the p-n junction 14 varies linearly in proportion to the pressure-sensitive membrane deflection 16.

In one example embodiment, during operation of the optical microphone 10 with sound under 70 dBSPL levels, the output of the optical microphone 110 without internal amplification using a commercial 1330 nm VCSELs was on the order of millivolts.

In one embodiment, the optical microphone 110 is provided access to pressure variations in the sample gas, yet provides a seal to prevent gas from entering or escaping from gas cell 102 other than by the opening 104.

In some embodiments, the optical microphone 110 collects pressure fluctuations within the ambient environment (i.e., noise) when the light source 106 is not producing radiation to determine spectral content of the pressure fluctuations within the ambient environment.

A control 120 receives signals from the detector 108 that represent the spectral content of the pressure fluctuations within the ambient environment. The control 120 adjusts a frequency of the radiation produced by the light source 106 to a frequency that conflicts less with the spectral content of the pressure fluctuations within the ambient environment.

In some embodiments, the photoacoustic sensor 100 may further comprise a light filter 116, which is positioned between the light source 106 and the gas cell 102 to filter the radiation into the gas cell. In some embodiments, a modulator 118 may be used to modulate the radiation generated by the light source 106 during detecting the sample gas. In one embodiment, the light filter 116 also provides a seal to prevent gas from entering or escaping from gas cell 102 other than by the opening 104.

As an example, during detecting an infrared light source 106 may be modulated to radiate the sample gas in the gas cell 102 to cause the sample gas within the gas cell 102 to heat and cool as incident infrared radiation is modulated. These temperature fluctuations in turn generate pressure waves, which may be detected by the optical microphone 118 which generates an electrical output voltage signals.

The electrical output voltage signals from the optical microphone 110 can be processed and analyzed to evaluate the properties or attributes of the sample gas sealed in the gas cell 102. As an example, by analyzing an obtained spectrum of the sample gas sealed in the gas cell 102, users may identify substances existing in the sample gas, and determine the concentration of the substances in the sample gas within the gas cell 102. Various known techniques may be used to detect the properties or attributes of the sample gas by using the photoacoustic sensor of the present application.

Other example embodiments relate to a method detecting a gas within a sample. The method includes providing a sample gas to an opening of a gas cell and using a control to direct a light source to emit radiation at the gas sample. The method further includes generating an output signal representative of pressure fluctuations of the radiated gas sample. The output signals are generated by (i) using a semiconducting laser to direct coherent light toward an pressure-sensitive membrane; and (ii) using the pressure-sensitive membrane to direct reflected light back toward the semiconducting laser to mix the reflected light with the coherent light within a cavity of the semiconducting laser such that a voltage level of a p-n junction within the semiconducting laser changes to provide the output signal.

In some embodiments, generating an output signal representative of pressure fluctuations of the radiated gas sample further includes providing DC power to the semiconducting laser with a current source such that when the semiconducting laser is above a lasing threshold a voltage is generated at the p-n junction. It should be noted that the reflected light undergoes phase changing as the pressure-sensitive membrane fluctuates due to pressure fluctuations from the radiated gas sample that act on the pressure-sensitive membrane.

Embodiments are contemplated where using a control to direct a light source to emit radiation at the gas sample includes using the control to direct the light source to emit radiation at a frequency that minimizes conflicting pressure fluctuations with the spectral content of the pressure fluctuations within the ambient environment.

While there has been described herein the principles of the application, it is to be understood by those skilled in the art that this description is made only by way of example and not as a limitation to the scope of the application. Accordingly, it is intended by the appended claims, to cover all modifications of the application which fall within the true spirit and scope of the application.

The invention claimed is:

1. A photoacoustic sensor comprising: a gas cell having an opening; a light source positioned outside the gas cell to generate radiation to radiate sample gas within the gas cell; a first membrane that is aligned with the opening of the gas cell to permit the sample gas to enter the gas cell;

and an optical microphone to detect the sample gas within the gas cell and to generate output electrical voltage signals in response to acoustic signals generated by pressure fluctuations of the radiated sample gas caused by the radiation, the optical microphone including a semiconducting laser that has a p-n junction within a cavity, the optical microphone further including a second membrane different from said first membrane, said second membrane comprising a pressure-sensitive membrane that receives coherent light emitted from the semiconducting laser and directs reflected light back toward the cavity, the phase of the reflected light being dependent upon a distance of the pressure-sensitive membrane from the cavity;

and wherein the second membrane of the optical microphone collects pressure fluctuations within the ambient environment when the light source that is positioned outside the gas cell is not producing radiation to determine spectral content of the pressure fluctuations within the ambient environment, and the photoacoustic sensor further comprises:

a control that receives the output electrical voltage signals from the optical microphone that represent the spectral content of the pressure fluctuations within the ambient environment, the control selects a frequency of the radiation produced by the light source that is positioned outside the gas cell so that the spectral content of the pressure fluctuations produced within the gas cell when subjected to the radiation conflict less with the spectral content of the pressure fluctuations within the ambient environment.

2. The photoacoustic sensor of claim 1, wherein the semiconducting laser is a diode laser.

3. The photoacoustic sensor of claim 1, wherein the semiconducting laser is a vertical cavity surface emitting laser.

4. The photoacoustic sensor of claim 1, wherein the pressure-sensitive second membrane flexes in response to pressure waves.

5. The photoacoustic sensor of claim 1, wherein the pressure-sensitive second membrane is formed of silicon dioxide.

6. The photoacoustic sensor of claim 1, wherein the pressure-sensitive second membrane includes a reflective layer formed of gold.

7. The photoacoustic sensor of claim 1, further comprising a current source for supplying power to the semiconducting laser such that when the semiconducting laser is above a lasing threshold, a voltage is generated at the p-n junction.

8. The photoacoustic sensor of claim 7, wherein the reflected light undergoes phase changing as the pressure-sensitive second membrane fluctuates due to acoustic pressure waves acting on the pressure-sensitive second membrane, and wherein the voltage at the p-n junction changes as the reflected light mixes with the coherent light in the cavity.

9. The photoacoustic sensor of claim 1, wherein the coherent light is a sinusoidal light wave that includes a maximum, a minimum and a midpoint between the maximum and the minimum, the pressure-sensitive second membrane being located at a distance from the aperture such that the sinusoidal light wave reaches the pressure-sensitive second membrane at the midpoint of the sinusoidal light wave.

10. The photoacoustic sensor of claim 9, wherein a voltage at the p-n junction varies linearly in proportion to the pressure-sensitive second membrane deflection.

11. The photoacoustic sensor of claim 1, wherein the semiconducting laser is surface mounted onto a substrate.

12. The photoacoustic sensor of claim 11, further comprising a bond pad mounted on the substrate, the bonding pad providing a current input to power the semiconducting laser and an output for measuring a voltage at the p-n junction.

13. The photoacoustic sensor of claim 1, further comprising a light filter positioned between the light source and the gas cell to filter the radiation radiated into the gas cell.

14. A method of detecting a gas within a sample contained within a gas cell, the method comprising: providing the sample to an opening of the gas cell through a first membrane; using a control to direct a light source that is external to the gas cell to emit radiation at the gas sample within the gas cell; and generating an output signal representative of pressure fluctuations of the radiated gas sample by using a semiconducting laser of an optical microphone to direct coherent light toward a second membrane different from said first membrane, said second membrane comprising a pressure-sensitive membrane and using said pressure-sensitive second membrane to direct reflected light back toward the semiconducting laser to mix the reflected light with the coherent light within a cavity of the semiconducting laser such that a voltage level of a p-n junction within the semiconducting laser changes to provide the output signal, And collecting via said second membrane of the optical microphone pressure fluctuations within the ambient environment when the light source that is positioned outside the gas cell is not producing radiation to determine spectral content of the pressure fluctuations within the ambient environment, and controlling via a control that receives the output electrical voltage signals from the optical microphone that represent the spectral content of the pressure fluctuations within the ambient environment, selection of a frequency of the radiation produced by the light source that is positioned outside the gas cell so that the spectral content of the pressure fluctuations produced within the gas cell when subjected to the radiation conflict less with the spectral content of the pressure fluctuations within the ambient environment.

15. The method of claim 14, wherein generating an output signal representative of pressure fluctuations of the radiated gas sample further includes providing DC power to the semiconducting laser with a current source such that when the semiconducting laser is above a lasing threshold a voltage is generated at the p-n junction.

16. The method of claim 14, wherein the reflected light undergoes phase changing as the pressure-sensitive second membrane fluctuates due to pressure fluctuations acting on the pressure-sensitive second membrane.

17. The method of claim 16, wherein using a control to direct a light source that is positioned outside the gas cell to emit radiation at the gas sample includes using a control to direct a light source to emit radiation at a frequency so that the spectral content of the pressure fluctuations produced within the gas cell when subjected to the radiation conflict less with the spectral content of the pressure fluctuations within the ambient environment.

18. A photoacoustic sensor comprising: a gas cell having an opening; a light source positioned outside the gas cell to generate radiation to radiate sample gas within the gas cell; a first membrane that is aligned with the opening of the gas cell to permit the sample gas to enter the gas cell;

and an optical microphone within the gas cell to detect the sample gas within the gas cell and to generate output electrical voltage signals in response to acoustic signals generated by pressure fluctuations of the radiated sample gas caused by the radiation, the optical microphone including:

a vertical cavity surface emitting laser that includes a p-n junction within a cavity; the optical microphone further including a second membrane different from said first membrane, said second membrane comprising an acoustic membrane that receives coherent light emitted from the vertical cavity surface emitting laser and directs reflected light back toward the cavity, the phase of the reflected light being dependent upon a distance of the acoustic second membrane from the vertical cavity surface emitting laser; wherein the acoustic second membrane flexes in response to pressure waves;

and a direct current source for supplying power to the vertical cavity surface emitting laser such that when the semiconducting laser is above a lasing threshold a voltage is generated at the p-n junction, wherein the reflected light undergoes phase changing as the acoustic second membrane fluctuates due to acoustic pressure waves acting on the acoustic second membrane, and wherein the voltage at the p-n junction changes as the reflected light mixes with the coherent light in the cavity of the vertical cavity surface emitting laser, and wherein the second membrane of the optical microphone collects pressure fluctuations within the ambient environment when the light source that is positioned outside the gas cell is not producing radiation to determine spectral content of the pressure fluctuations within the ambient environment, and the photoacoustic sensor further comprises:

a control that receives the output electrical voltage signals from the optical microphone that represent the spectral content of the pressure fluctuations within the ambient environment, the control selects a frequency of the radiation produced by the light source that is positioned outside the gas cell so that the spectral content of the pressure fluctuations produced within the gas cell when subjected to the radiation conflict less with the spectral content of the pressure fluctuations within the ambient environment.

19. The photoacoustic sensor of claim 18, wherein the coherent light is a sinusoidal light wave that includes a maximum, a minimum and a midpoint between the maximum and the minimum, the acoustic second membrane being located at a distance from the vertical cavity surface emitting laser such that the sinusoidal light wave reaches the acoustic second membrane at the midpoint of the sinusoidal light wave, and wherein a voltage at the p-n junction varies linearly in proportion to the acoustic second membrane deflection.

\* \* \* \* \*